ial(12) United States Patent  
Gunzert-Marx et al.

(10) Patent No.: US 7,875,846 B2  
(45) Date of Patent: Jan. 25, 2011

(54) MOUNTING DEVICE FOR PHANTOM, METHOD FOR QUALITY MONITORING OF A PARTICLE THERAPY SYSTEM, AND PARTICLE THERAPY SYSTEM

(75) Inventors: Konstanze Gunzert-Marx, Erlangen (DE); Sophia Knop, Erlangen (DE); Tim Use, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 317 days.

(21) Appl. No.: 12/074,029

(22) Filed: Feb. 28, 2008

(65) Prior Publication Data

US 2008/0219411 A1 Sep. 11, 2008

(30) Foreign Application Priority Data

Mar. 7, 2007 (DE) ........................ 10 2007 011 153

(51) Int. Cl.  
*G01D 18/00* (2006.01)

(52) U.S. Cl. .................................................. 250/252.1

(58) Field of Classification Search ............. 250/252.1, 250/306, 307, 370.07, 393; 378/18, 48, 50, 378/65, 204, 207, 208  
See application file for complete search history.

(56) References Cited

U.S. PATENT DOCUMENTS

| 5,095,499 | A | 3/1992 | Wentz |
| 5,481,587 | A | 1/1996 | Mazess |
| 5,769,779 | A | 6/1998 | Alderson |
| 6,207,952 | B1 | 3/2001 | Kan et al. |
| 6,231,231 | B1 * | 5/2001 | Farrokhnia et al. .......... 378/207 |
| 6,670,618 | B1 * | 12/2003 | Hartmann et al. ........ 250/491.1 |
| 2005/0013406 | A1 | 1/2005 | Dyk et al. |
| 2006/0002511 | A1 * | 1/2006 | Miller et al. .................. 378/65 |

FOREIGN PATENT DOCUMENTS

| DE | 29 03 023 | 7/1980 |
| DE | 200 09 714 | 11/2001 |
| EP | 1 062 912 A1 | 12/2000 |

OTHER PUBLICATIONS

German Office Action dated Sep. 6, 2007 for DE 10 2007 011 153. 5-54 with English translation.  
European Search Report dated Jul. 15, 2008 with English translation.  
2000 Optics and Optical Instruments Catalog, Edmund Industrial Optics Catalog 2000, Barrington, NJ XP002486772, p. 106.

* cited by examiner

*Primary Examiner*—David P Porta  
*Assistant Examiner*—Mark R Gaworecki  
(74) *Attorney, Agent, or Firm*—Brinks, Hofer, Gilson & Lione

(57) ABSTRACT

A mounting device for phantoms for use in quality monitoring of a radiation therapy system is described. The mounting device is adapted such that a plurality of phantoms can be placed replicably in a defined position on the mounting device. A quality assurance procedure is performed by placing a plurality of phantoms on a mounting device, each phantom at a predefined position; positioning the mounting device in the radiation therapy system, so that one of the phantoms is located in a position intended for performing a quality monitoring procedure; and performing the procedure using one or more of the phantoms.

13 Claims, 4 Drawing Sheets

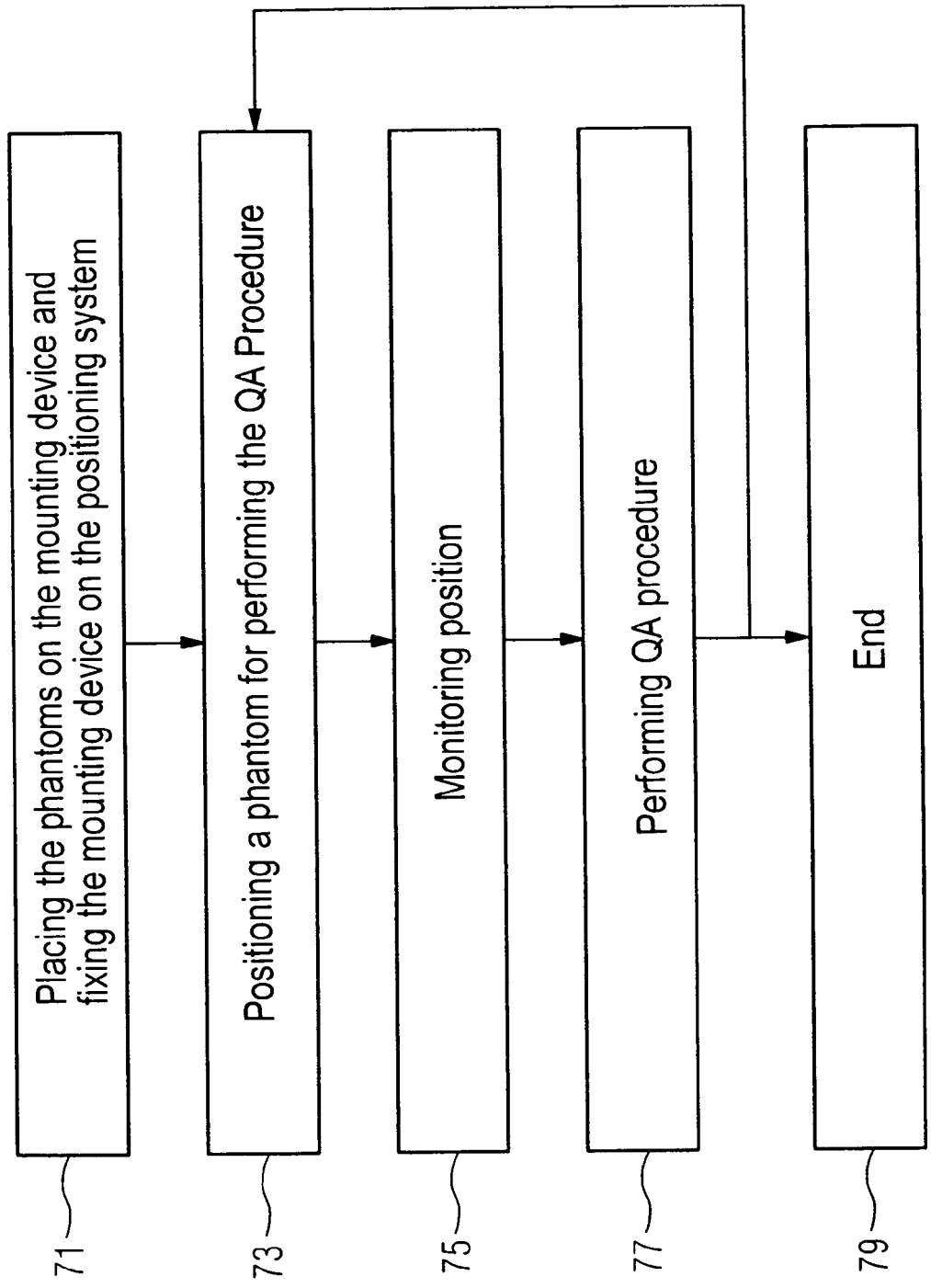

MOUNTING DEVICE FOR PHANTOM, METHOD FOR QUALITY MONITORING OF A PARTICLE THERAPY SYSTEM, AND PARTICLE THERAPY SYSTEM

The present application claims priority to German patent application No.: DE 10 2007 011 153.5, filed on Mar. 7, 2007, which is incorporated herein by reference.

TECHNICAL FIELD

This application relates to quality monitoring in a radiation therapy system, a mounting device for phantoms, and to a radiation therapy system or particle therapy system for performing the same.

BACKGROUND

Radiation therapy is employed for the treatment of tumor tissue in humans. Ions such as protons, helium ions, pions, carbon ions, or other types of ions can be employed for the radiation treatment. Radiation treatment with ions is characterized by the property that the penetration depth of the radiation into human tissue can be controlled more precisely than in other types of radiation treatment. This makes more precisely targeted radiation treatment of the tumor possible, and the surrounding tissue that is to be spared from damage can be better protected from the radiation.

The ions are accelerated to high energies in an accelerator system which, for example, includes a synchrotron or cyclotron, and are aimed in a beam at the body to be treated. The beam is deflected and controlled by a magnet system. Beam properties that are essential and relevant for safety are dependent on the settings of parameters at the system itself. These characteristics include, for example, the beam diameter, the beam position, and the energy of the beam. Such characteristics are measured, for instance, daily or weekly.

Monitoring the beam properties is performed with so-called phantoms. Such phantoms are irradiated with the particle beam, and the interaction of the particle beam with the phantom is measured or detected. This can be done, for example, by using photographic films that are exposed as a result of the irradiation by the particle beam, and allow conclusions to be drawn about the parameters of the particle beam. Detectors of other types, such as ionization chambers or thimble chambers, may also be employed.

Monitoring various beam parameters requires the use of many different phantoms. Until now, these phantoms have been individually and successively positioned manually relative to the beam. For each QA procedure, whichever phantom is needed is put in a defined spatial position relative to the beam so that for different phantoms, the positioning has to be performed each time and requires repetitive manual intervention. The expense in terms of time, labor, and cost is considerable.

SUMMARY AND DESCRIPTION

A mounting device for phantoms for performing QA procedures in a radiation therapy system is described. The mounting device for phantoms is used for quality monitoring of a radiation therapy system, in particular a particle therapy system. The mounting device is configured such that a plurality of phantoms may be replicably placed in a defined position on the mounting device.

A plurality of different phantoms may be precisely and replicably positioned on the mounting device. The positioning of the various phantoms in space can then be performed by positioning of the mounting device. As a result of positioning the mounting device in space, the various phantoms can each be positioned and oriented in the position in which the QA procedure may then be performed. This reduces the number and complexity of the manual interventions.

Depending on the design of the phantom, particular properties of the particle beam can be monitored, such as the range, and hence the energy of the particle beam, the extent or beam width of the particle beam, or the position of the particle beam. Depending on the characteristics of the particular phantom, the evaluation of the monitored beam parameters can be performed during the associated QA procedure ("on-line"), or after the associated QA procedure has been performed ("off-line").

Because the phantoms can be placed replicably on the mounting device, the same arrangement of phantoms may be repeatedly achieved even if the phantoms are replaced or the mounting device with the phantoms is disassembled.

In an aspect, the mounting device may have a fixation device for connection to a positioning system. The positioning system may be the patient positioning system which, in a radiation therapy system, may already be present in treatment chamber. Because of the fixation device, precise, replicable securing of the mounting device to the positioning system may be repeatedly performed. The positioning in space of the mounting device with the phantoms may be performed using the positioning system. This may be performed automatically providing that control parameters for the positioning system are stored, for example, in a computer memory in a control unit for the positioning system.

The mounting device may be coupled with the fixation device of a robot arm that may otherwise be used for positioning a treatment table. Alternatively, the coupling can be directly to the robot arm, by removing the treatment table; or, to the treatment table.

The control parameters of the positioning device are adapted to the particular phantom arrangement on the mounting device, so that a phantom may be positioned at a location in space that is suitable for the appropriate QA procedure. Because the phantoms can be disposed replicably on the mounting device, the control parameters for the mounting device may not need to be re-determined, except when a different arrangement of phantoms on the mounting device is chosen. The control parameters may take the orientation of the treatment beam into account.

In an aspect, the mounting device is a substantially planar platform. A planar platform is typically adapted to the planar geometry of a treatment table, and may be provided with a fixation device for connecting the platform to the patient positioning system.

In an aspect, the platform has a regular pattern of holes. As a result of this pattern of holes, the phantoms can be disposed simply and replicably at a defined position on the platform, for instance by being snapped into place using guide pins, or the like.

In another aspect, the mounting device has at least one position marking, to be used in monitoring the correct positioning of the mounting device in space. Since the defined position of the phantoms on the mounting device is then known, it is also possible to monitor the position of the phantoms in space indirectly, thus enhancing both the quality and safety of a QA procedure.

A method for quality monitoring of a radiation therapy system includes the steps of: placing a phantom on a mounting device having the capability of accepting at least two phantoms, the phantom being placed at a predefined position;

positioning the mounting device in the radiation therapy system, so that the phantom is located in a position intended for performing quality monitoring; performing the quality monitoring with the phantom; and, repeating the process until quality monitoring procedure has been performed with one or more phantoms.

By the use of a mounting device for a plurality of phantoms, the quality monitoring may be simplified. The positioning of each of a plurality of the phantoms is done using a successive positioning of the mounting device so that, in the performance of the quality monitoring, the repeated manual replacement of the individual phantoms may be avoided. Automating the successive positioning of different phantoms saves time.

In an aspect, the mounting device is positioned by a positioning system, in particular a patient positioning system. In this way, positioning the mounting device spatially can be performed automatically, and precisely. The control parameters for the positioning system may be stored in a computer memory associated with a processor in a control unit and can be adapted to the predefined position of the phantoms on the mounting device. Thus, performing a plurality of QA procedures can be substantially automated; manual operations may be reduced to, for example, mounting the phantoms on the mounting device, and initiating the procedure.

In another aspect, after the positioning of the mounting device, the position of the mounting device or of the respective phantom relative to a spatially fixed coordinate system may monitored, for example, with the aid of a laser device. This may for instance be a system of laser beams or fans that indicate a specific coordinate point in space, such as the isocenter of the treatment chamber. However, the laser beams may also be used to indicate coordinate points in space that define the set-point position of a position marking on the mounting device. Monitoring the correct position can be done, for example, visually or automatically using suitable detectors, which may be photodetectors, or a digital camera. However, it is also possible to track and monitor the coordinates of the positioning system at a control panel.

DESCRIPTION

Exemplary embodiments may be better understood with reference to the drawings, but these examples are not intended to be of a limiting nature. Like numbered elements in the same or different drawings perform equivalent functions. When a specific feature, structure, or characteristic is described in connection with an example, it will be understood that one skilled in the art may effect such feature, structure, or characteristic in connection with other examples, whether or not explicitly stated herein.

The examples of diseases, syndromes, conditions, and the like, and the types of treatment protocols described herein are by way of example, and are not meant to suggest that the method and apparatus is limited to those named, or the equivalents thereof. As the medical arts are continually advancing, the use of the methods and apparatus described herein may be expected to encompass a broader scope in the diagnosis and treatment of patients.

Embodiments of this invention may be implemented in hardware, firmware, software, or any combination thereof, and may include instructions stored on a machine-readable medium, which may be read and executed by one or more processors.

Figure 1:
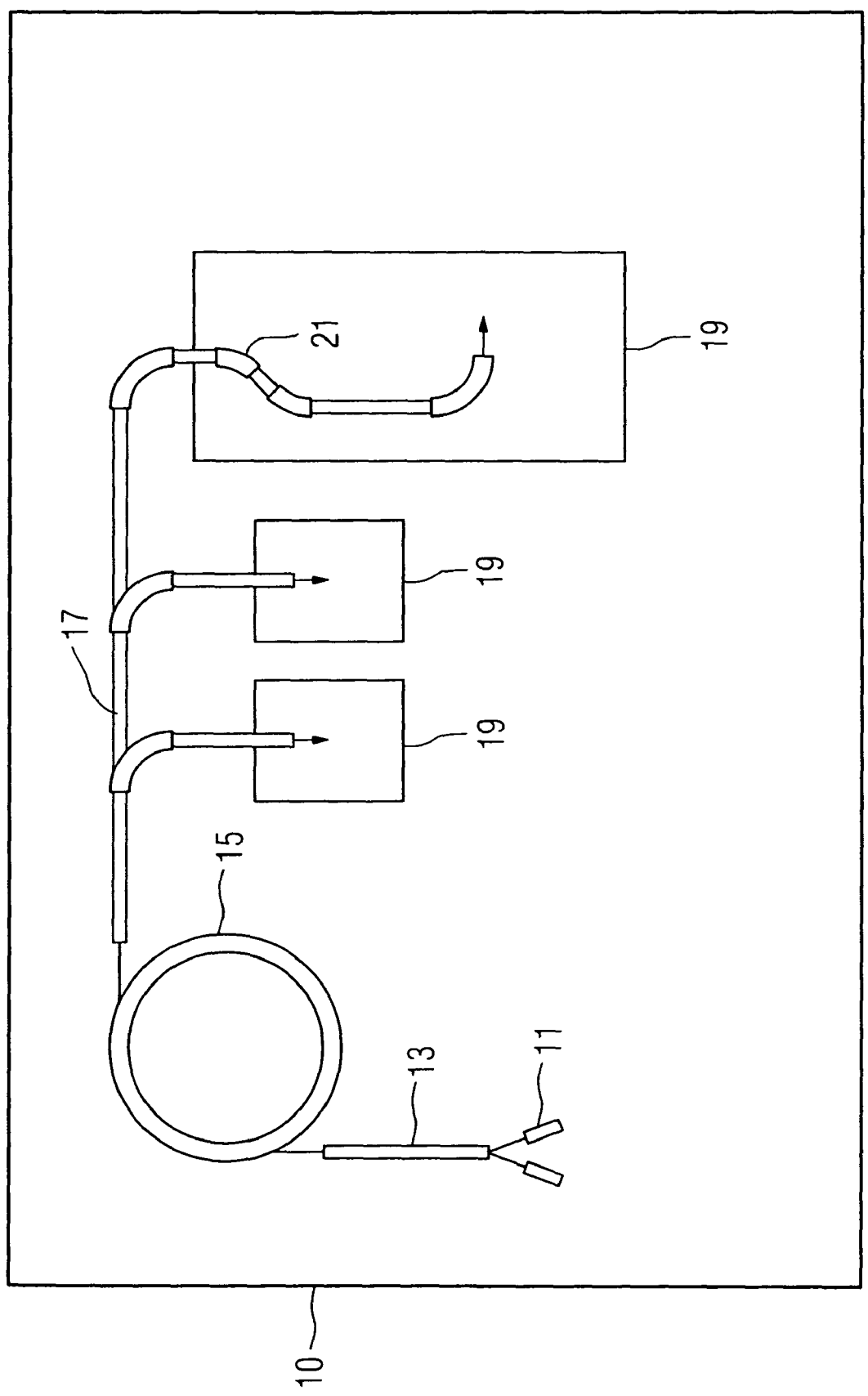
FIG. 1 shows a schematic overview of the construction of a particle therapy system.

FIG. 1 shows a schematic overview of the construction of a particle therapy system 10. In a particle therapy system 10, radiation treatment of diseased tissue involving tumors, for example, may be performed with a particle beam. Ions, such as protons, pions, helium ions, carbon ions, or other types of ions, may be used.

Such particles may be generated in a particle source 11 and accelerated in a pre-accelerator 13, such as a linear accelerator (LINAC). The particles may be introduced into a particle accelerator 15, such as a Synchrotron or Cyclotron, in which the particles are accelerated to energies of the kind used for the radiation treatment. Once the particles leave the accelerator 15, a high-energy-beam transport system 17 carries the particle beam to the desired treatment rooms or chambers 19. In a treatment chamber 19, the accelerated particles are aimed at a body. Depending on the design, the beam has a fixed direction (in so-called "fixed-beam" chambers), or may have varying directions by using a movable rotatable gantry 21. Although this basic construction of a particle therapy system 10 is typical for many particle therapy systems, other configurations may equally be used.

Figure 2:
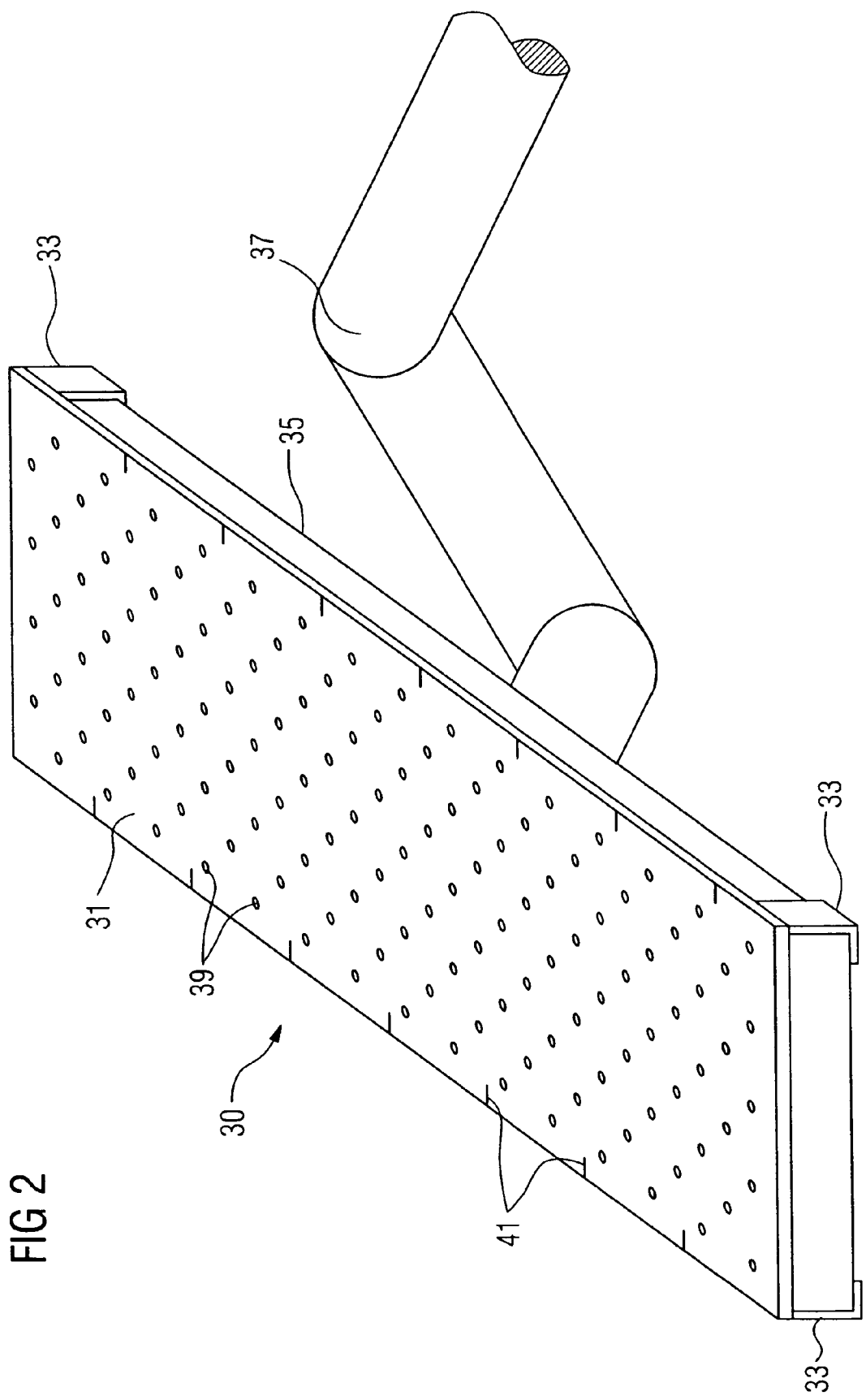
FIG. 2 shows perspective view of an embodiment of a mounting device for phantoms.

FIG. 2 shows a perspective view of a mounting device 30 for phantoms on which various phantoms may be disposed at predefined positions. The mounting device 30 may be a substantially planar platform 31. In this example, the mounting device 30 has fixation devices 33 at each corner, with which the mounting device 30 can be releasably coupled to a treatment table 35. Other attachment or clamping mechanisms may be used.

The treatment table 35 may be positioned in the treatment chamber via a positioning system 37, only the arms of which are shown. The positioning system 37 may be, for example, a robot arm and may interface with the treatment table 35 on the underside thereof. Using the positioning system 37 which, in this example, is the patient positioning system, the treatment table 35 may be positioned at a desired location in the treatment chamber.

The fixation device 33 as shown is clamped around the treatment table 35. Other connections are possible.

Alternatively, the mounting device may interface directly with the positioning system for the treatment table 35. The treatment table 35 may be removed and the mounting device 30 coupled to the positioning system for the treatment table using a fixation device mounted, for example, on the underside of the mounting device 30.

Using the positioning system 37, the mounting device 30 may be moved to a predefined position in space. By using the fixation device 33, the mounting device 30 can be repetitively aligned in the same relative position to the treatment table 35.

The docking of the positioning system 37, which may be a robot arm, to the mounting device 30 can also be done automatically. For instance, the mounting device 30 can be temporarily supported on a shuttle cart, so that a user can easily bring the mounting device into the treatment chamber. The positioning system 37 can then dock automatically onto the mounting device 30 and remove the mounting device 30 from the shuttle cart and orient it at the desired position in space.

The planar surface 31 of the mounting device 30 may have a plurality of indentations 39 in the form of holes, which may be distributed in a regular pattern over the plane platform 31. The indentations 39 may be used for disposing phantoms on the plane platform in a predefined position. The phantoms may, for example, have protrusions on their underside that are adapted to interface with the indentations and with which the phantoms can be disposed at the desired position on the plane platform 31.

The plane platform 31 may also have position markings 41, with which correct positioning of the mounting device 30 in space can be monitored. This may be achieved, for example, by a system of laser beams, which are disposed in the treatment chamber and with which defined spatial locations in the treatment chamber can be marked. The correct positioning of the mounting device 30 in space may be monitored by means of visual or automatic calibration of the position markings 41 using the laser beams.

Figure 3:
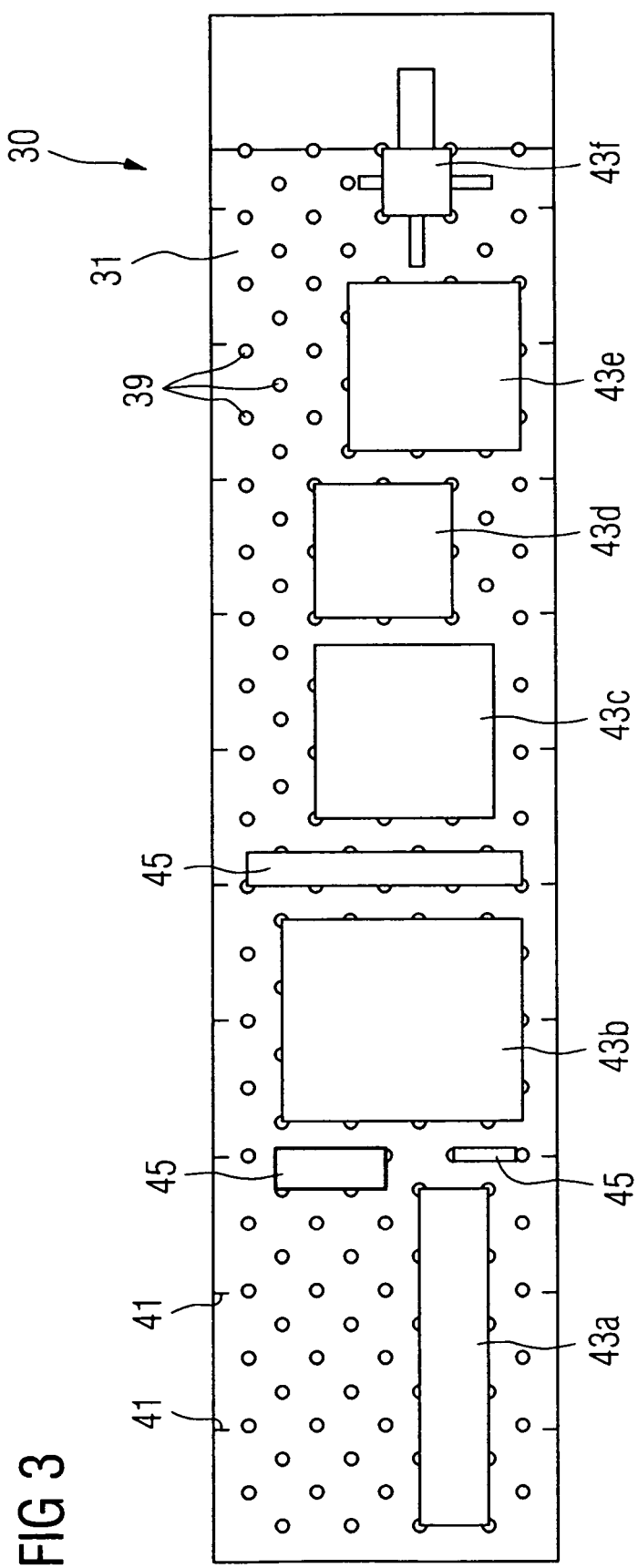
FIG. 3 shows plan view of the mounting device of FIG. 2 on which a plurality of phantoms are disposed; and, FIG. 4 shows a schematic overview of one embodiment of the steps in a method for quality monitoring.

FIG. 3 shows a plan view on the plane platform 31, on which various phantoms 43a . . . 43f are disposed, each of which is used for performing a specific QA procedure. In addition to the phantoms 43a . . . 43f, other components 45, which may be used for operating the phantoms, such as power packs, converters, multiplug strips, and the like, can be disposed on the plane platform 31.

FIG. 4 shows a schematic overview of the steps in a method for quality monitoring. The method includes the steps of: positioning the phantoms on the mounting device (step 71); positioning the mounting device in space using the positioning system (step 73); optionally, verifying the position of the phantom (step 75); and, performing one or more quality assurance procedures (step 77). The steps of positioning, optionally verifying, and performing quality assurance procedures may be repeated until all of the desired procedures have been performed, and the process is concluded (step 79).

In step 71, the phantoms may be positioned on the mounting device. The phantoms may remain on the mounting device until a phantom, has to be replaced. Thus, performing the QA procedures with the phantoms may involve positioning of the mounting device with the phantoms, as in FIG. 3, on a positioning system, without having to individually place the phantoms each time the QA procedures are performed. The remainder of the method of QA procedures can then be performed automatically.

In step 73, the mounting device may be positioned in space with the aid of the positioning system in such a way that one of the phantoms is positioned at a location in the treatment chamber for performing the QA procedure. For that purpose, the necessary control parameters may be stored in memory in a control unit for the positioning system.

In step 75, monitoring of the position is optionally done, for instance, using the position markings shown in FIG. 2, or using a laser system, disposed in the treatment chamber, for projecting laser beams that indicate certain coordinates in space. The positioning of the phantoms may also be determined by the robot system using the coordinates of the mounting table, and this may be used as a further quality assurance step.

While the method disclosed herein has been described and shown with reference to particular steps performed in a particular order, it will be understood that these steps may be combined, sub-divided, or reordered to from an equivalent method without departing from the teachings of the present invention.

Although only a few exemplary embodiments of this invention have been described in detail above, those skilled in the art will readily appreciate that many modifications are possible in the exemplary embodiments without materially departing from the novel teachings and advantages of the invention. Accordingly, all such modifications are intended to be included within the scope of this invention as defined in the following claims.

The invention claimed is:

1. An apparatus for quality monitoring of a particle therapy system, the apparatus comprising:
   a mounting device adapted to receive a plurality of phantoms having differing characteristics, each phantom having a defined position on the mounting device and each phantom being adapted to monitor a different property of a particle beam; and
   a movable positioning system adapted to position the mounting device into a plurality of different positions, bringing the plurality of phantoms mounted on the mounting device into a plurality of defined positions relative to the particle beam,
   wherein the mounting device comprises a fixation device adapted to interface with the positioning system.

2. The apparatus of claim 1, wherein the positioning system is a patient positioning system.

3. The apparatus of claim 1, wherein the mounting device is a structure with a substantially planar surface.

4. The apparatus of claim 3, wherein the planar surface has a pattern of holes, for snapping the plurality of phantoms into place at defined positions.

5. The apparatus of claim 4, wherein the holes form a regular pattern.

6. The apparatus of claim 1, wherein the mounting device has a position marking.

7. A method for quality monitoring of a particle therapy system, the method comprising:
   placing a plurality of phantoms on a mounting device at predefined positions, each phantom being adapted to monitor a different property of a particle beam;
   positioning the mounting device in the particle therapy system with a positioning system, so that the phantoms are located in a position for performing a quality monitoring procedure; and
   performing the quality monitoring procedure using the phantoms;
   wherein the mounting device is positioned into a plurality of different positions, sequentially positioning at least two of the plurality of phantoms at different predefined spatial positions to perform two different quality monitoring procedures for different properties of the particle beam.

8. The method of claim 7, wherein the positioning system is a patient positioning system.

9. The method of claim 7, wherein control parameters for positioning the mounting device are stored in memory in a control unit of the positioning system.

10. The method of claim 7, wherein after the positioning of the mounting device, the position of the mounting device relative to a spatially fixed coordinate system is monitored, using at least one position marking on the mounting device.

11. A medical treatment system, the system comprising:
    a particle therapy apparatus, the particle therapy apparatus further comprising:
       a mounting device adapted to simultaneously receive a plurality of phantoms having differing characteristics, each phantom having a selectable position on the mounting device and each phantom being adapted to monitor a different property of a particle beam, and
       a movable positioning device adapted to position the mounting device into a plurality of different positions, bringing the plurality of phantoms mounted on the mounting device into a plurality of defined positions relative to the particle beam, wherein the mounting device is adapted to interface with the movable positioning device.

12. The medical treatment system of claim 11, wherein the particle therapy apparatus further comprises an ion generator and an ion accelerator to produce an ion beam.

13. The medical treatment system of claim 11, wherein the system is configured to:

position the mounting device in the particle therapy apparatus, so that the phantom is located in a position intended for performing a quality monitoring procedure; and perform the quality monitoring procedure using the phantom, and wherein at least two of the plurality of phantoms are positioned sequentially at a predefined spatial position.

* * * * *